United States Patent
Abad et al.

(10) Patent No.: US 6,523,556 B2
(45) Date of Patent: Feb. 25, 2003

(54) PORTABLE CLEANING APPARATUS FOR GAS DISTRIBUTION TUBE

(75) Inventors: Glen Silva Abad, Placentia, CA (US); Stanley Bean, Cypress, CA (US); Ralph Edward Jaffke, Lakewood, CA (US); Joanne McLaughlin, Long Beach, CA (US); Rick Osterman, Long Beach, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 196 days.

(21) Appl. No.: 09/759,479

(22) Filed: Jan. 12, 2001

(65) Prior Publication Data

US 2002/0092549 A1 Jul. 18, 2002

(51) Int. Cl.[7] .................................................. B08B 3/04
(52) U.S. Cl. .............................. 134/166 C; 134/169 C; 134/168 C; 134/169 R
(58) Field of Search .......................... 134/166 R, 166 C, 134/169 R, 169 C, 168 R, 168 C, 167 R, 167 C, 22.1, 22.11, 22.12, 22.13, 22.14, 22.15, 22.16, 22.17, 22.18, 22.19

(56) References Cited

U.S. PATENT DOCUMENTS

| 2,425,848 | A | | 8/1947 | Vawter |
| 3,214,867 | A | | 11/1965 | Henning |
| 3,765,050 | A | * | 10/1973 | Van Allman et al. |
| 3,871,826 | A | * | 3/1975 | Bakay |
| 3,948,679 | A | * | 4/1976 | Lewis |
| 4,289,091 | A | | 9/1981 | Warner |
| 4,333,773 | A | * | 6/1982 | Fjallstrom |
| 4,398,552 | A | * | 8/1983 | Tanaka et al. |
| 4,750,941 | A | * | 6/1988 | Gerich |
| 4,863,555 | A | * | 9/1989 | John, Jr. et al. |
| 4,991,608 | A | | 2/1991 | Schweiger |
| 5,007,444 | A | | 4/1991 | Sundholm |
| 5,087,295 | A | * | 2/1992 | Gross et al. |
| 5,159,956 | A | * | 11/1992 | Kurihara |
| 5,213,119 | A | | 5/1993 | Kusz et al. |
| 5,416,947 | A | | 5/1995 | Jaffe |
| 5,419,349 | A | | 5/1995 | Swain |
| 5,678,584 | A | | 10/1997 | O'Brien |
| 5,680,877 | A | | 10/1997 | Edstrand et al. |
| 5,738,824 | A | * | 4/1998 | Pfeifer |
| 5,819,770 | A | * | 10/1998 | Randall et al. |
| D409,732 | S | | 5/1999 | Maddux et al. |
| 5,944,045 | A | * | 8/1999 | Allen et al. |
| 6,311,703 | B1 | * | 11/2001 | Webster et al. |
| 6,450,182 | B2 | * | 9/2002 | Fillip et al. |

FOREIGN PATENT DOCUMENTS

| SU | 280168 | * | 9/1970 |
| SU | 627871 | * | 8/1978 |
| SU | 1003941 | * | 3/1983 |

* cited by examiner

Primary Examiner—Frankie L. Stinson
(74) Attorney, Agent, or Firm—Stetina Brunda Garred & Brucker

(57) ABSTRACT

A portable flushing apparatus for cleaning the interior of a gas distribution tube. The apparatus includes a first reservoir structure housing a first solvent an a first conduit leading therefrom for selectively transporting solvent to the interior of the tube to be cleaned. A second reservoir structure houses a second solvent generally employed in a final cleaning flush, and has a second conduit leading therefrom for selectively transporting solvent to the interior of the tube. A gas supply conduit is included for selectively transporting purging gas to the interior of the tube. A downstream conduit collects or for releases for testing fluid from the tube. The entire apparatus can include a wheeled carrier. A liquid collector can be situated beneath the gas distribution tube for capturing any spilled solvent

10 Claims, 2 Drawing Sheets

PORTABLE CLEANING APPARATUS FOR GAS DISTRIBUTION TUBE

STATEMENT RE: FEDERALLY SPONSORED RESEARCH/DEVELOPMENT

STATEMENT OF GOVERNMENT RIGHTS

This invention was made with Government support under contract F33657-87-C-2000 awarded by the United States Air Force. The Government has certain rights in this invention.

CROSS-REFERENCE TO RELATED APPLICATIONS (Not Applicable)

BACKGROUND OF THE INVENTION

The present invention relates in general to equipment for cleaning gas distribution tubes such as those used in aircraft oxygen tubing, and in particular to a portable flushing apparatus including solvent reservoirs with controlled conduits therefrom safely carrying solvent to tubing to be cleaned and thereafter collecting the solvent and providing gas purging to assure environmental protection.

Specialized cleaning capabilities for certain applications embodying gas distribution tubing, as especially exemplified in-aircraft oxygen system tubes, require precision cleansing to assure non-adulterated gas flow. Traditionally, such cleansing has been accomplished by removing such tubing and taking it to an off-site location where ozone depleting solvents such as trichlorotrifluroethane were introduced and flushed through the tubes which thereafter were returned for reinstallation into the aircraft. While such chemicals are very effective in cleaning the tubing, their apparent danger to the atmosphere precludes continued use. As a result, other solvents are being developed for equal effectiveness but with less environmental danger.

While safer chemicals can accomplish tube cleansing, the actual cleaning procedure still is delegated to a site away from affected aircraft because no on-site equipment is currently available for adequately performing high quality cleansing as required for tubing providing aircraft oxygen delivery. In addition to general inconvenience, such off-site treatment causes increased turn-around time for completing each work product, increased costs for labor, product transportation and delivery, and the like. It is therefore apparent that a need is present for on-site equipment to accomplish proper and effective tube cleanliness. Accordingly, a primary object of the present invention is to provide a portable, on-site operable, flushing apparatus for cleaning the interior of a gas distribution tube.

Another object of the present invention is to provide a portable flushing apparatus wherein solvent and gas flushing assures end-product purity.

Yet another object of the present invention is to provide a portable flushing apparatus wherein capture of errant volatile materials is addressed.

These and other objects of the present invention will become apparent throughout the description thereof which now follows.

BRIEF SUMMARY OF THE INVENTION

The present invention is a portable flushing apparatus for cleaning the interior of a gas distribution tube such as employed in aircraft oxygen tubing. The apparatus comprises a first reservoir structure for housing a first solvent generally employed for initial flushing. This first reservoir structure has a first conduit leading therefrom in communication with a first end of the gas distribution tube to be cleaned for transporting fluid from the reservoir structure for selective delivery to the interior of the tube. A second reservoir structure is provided for housing a second solvent generally employed in a final cleaning flush. This second reservoir structure has a second conduit leading therefrom in communication with the first end of the gas distribution tube for transporting fluid therein from the second reservoir structure for selective delivery to the interior of the tube. A gas supply conduit is included and has a first end connectable to a gas supply line and a second end in communication with the first end of the gas distribution tube for transporting gas in the conduit for selective delivery to the interior of the tube. A downstream conduit is provided for communication with a second end of the gas distribution tube for collecting fluid therefrom or for releasing fluid therefrom through a collection port. The entire apparatus can include a wheeled carrier. Preferably, a liquid collector is situated to be beneath the gas distribution tube for capturing any spilled solvent during flushing of the tube. Additionally, the apparatus also preferably includes an exit conduit situated to receive and selectively transport therethrough collected gas to an exit port which is intended to be in communication with an adsorption filter for capturing volatile compounds.

Because of its portability, the present apparatus can be positioned at or near an aircraft being serviced such that the aircraft oxygen tubing can be removed and engaged with the apparatus for immediate cleaning and verification of cleanliness on-site and thereafter returned to the aircraft. Simultaneously, all materials employed in the cleaning process are safely retained to thereby protect the environment.

BRIEF DESCRIPTION OF THE DRAWING

An illustrative and presently preferred embodiment of the invention is shown in the accompanying drawings in which.

DETAILED DESCRIPTION OF THE INVENTION

Figure 1:
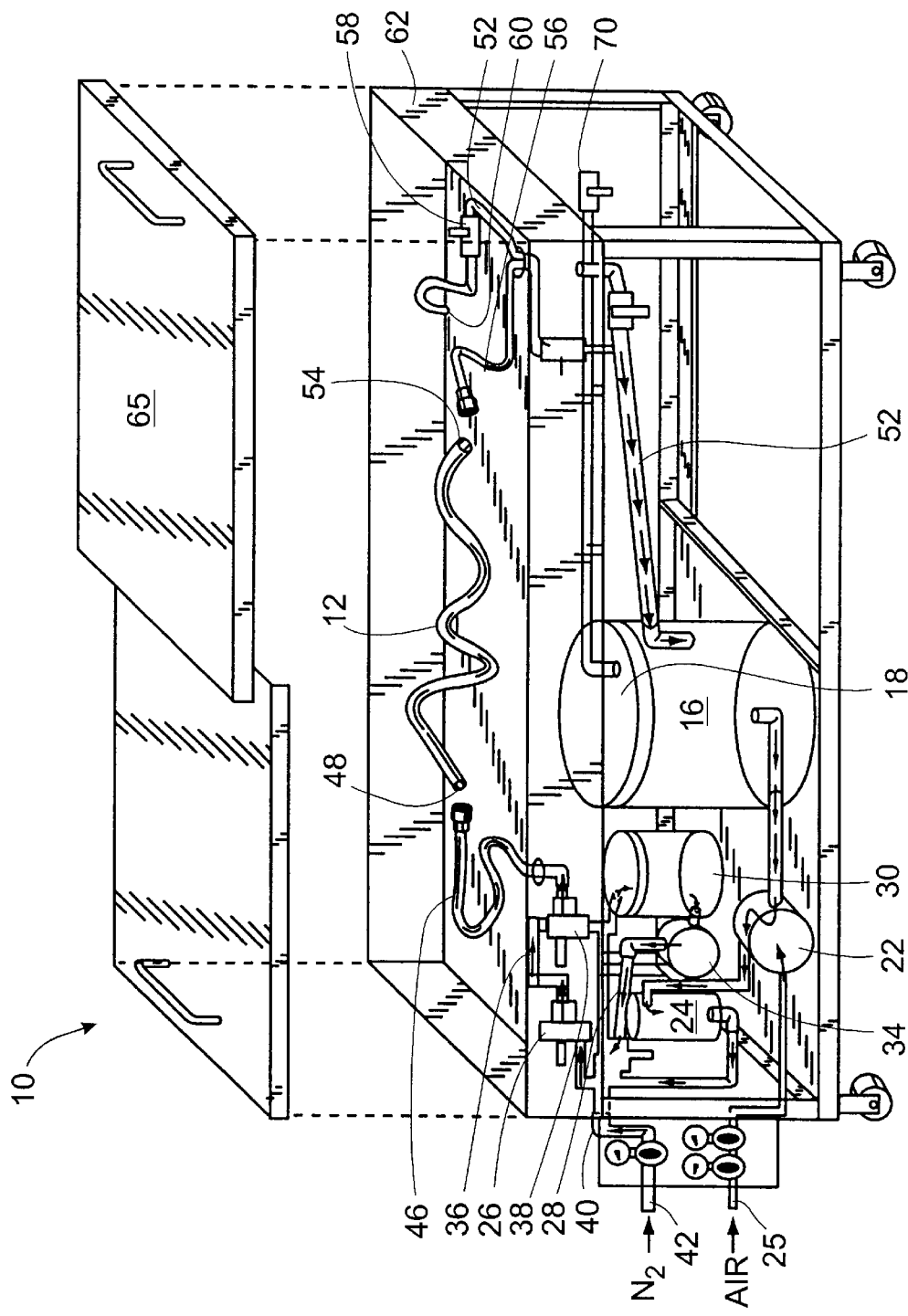
FIG. 1 is a perspective schematic view of an open portable flushing apparatus for cleaning the interior of a gas distribution tube.
Figure 2:
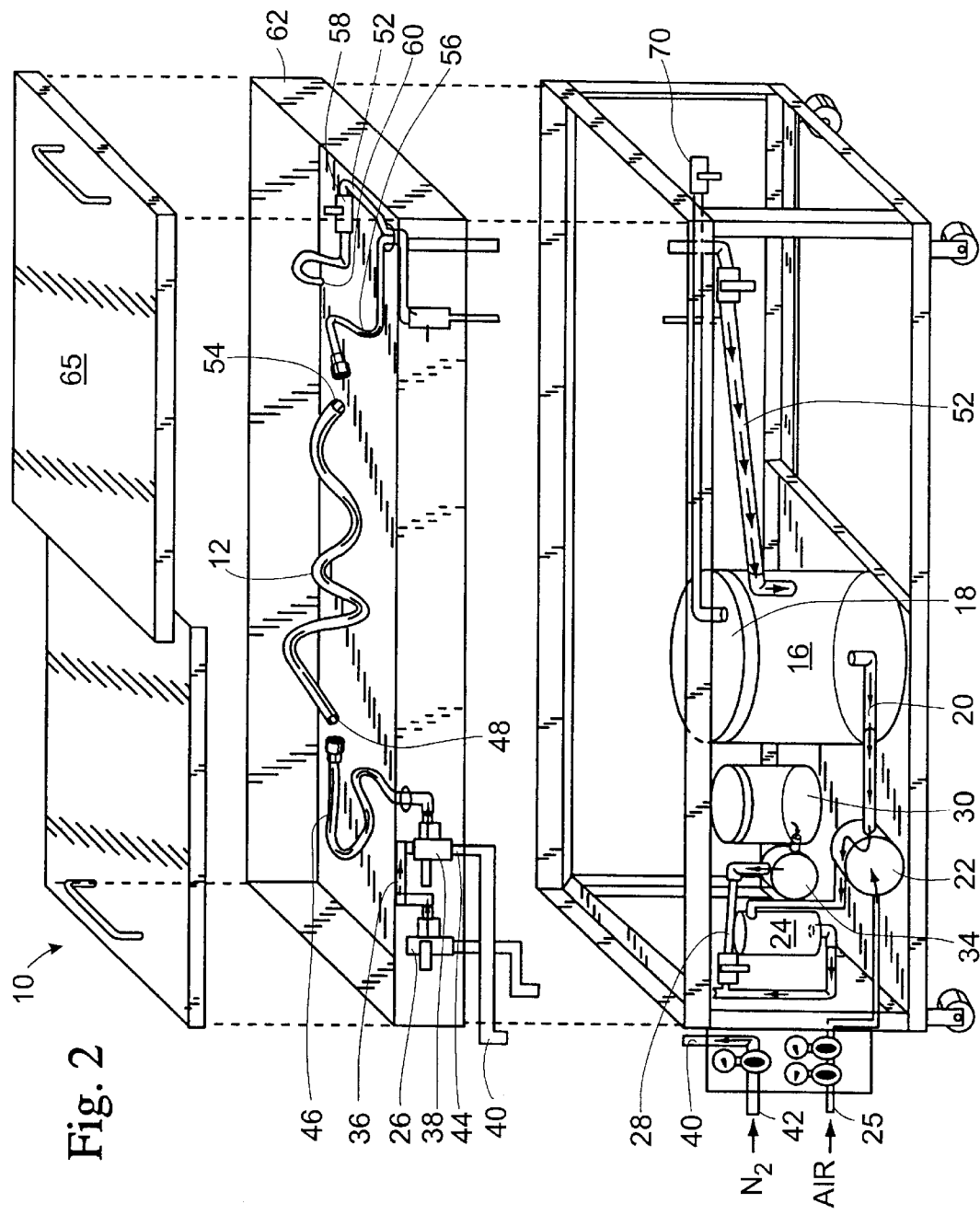
FIG. 2 is an exploded perspective schematic view of the apparatus of FIG. 1.

Referring to FIGS. 1 and 2, a portable flushing apparatus 10 for cleaning the interior of a gas distribution tube 12 such as that used in aircraft oxygen systems is shown. A hand-movable, wheeled-frame carrier 14 provides portability to the apparatus 10 to thereby permit on-site use. A first reservoir structure 16 having a sealed cover 18 is provided for housing a first solvent, and has a first conduit 20 leading therefrom for transporting therein via a first conventional air-driven diaphragm pump 22 the first solvent through a conventional fibrous filter 24 to a selectively openable and closable first input port of a conventional first three-way valve 26 to which the distal end of the first conduit 20 leads. In similar fashion a second conduit 28 leads from a second reservoir structure 30 having a sealed cover 32 and designated for housing a second solvent. The second conduit 28 transports therein via a second conventional air-driven diaphragm pump 34 the second solvent to a selectively openable and closable second input port of the first three-way valve 26 to which the distal end of the second conduit 28 leads. Air for the pumps 22, 28 is introduced through the air input 25.

Disposed downstream from the first three-way valve 26 and connected thereto by a third conduit 36 leading from a selectively openable and closable outlet port of the first three-way valve 26 is a conventional second three-way valve 38 such that the distal end of the third conduit 36 is connected to a first input port of the second three-way valve 38. Also provided is a gas supply conduit 40 having a first end 42 connectable to a gas supply line (not shown) and a second end 44 connected to a selectively openable and closable second input port of the second three-way valve 38. A first flexible hose 46 leads from an outlet port the second three-way valve 38 for connection via a conventional quick-disconnect fitting to a first end 48 of the gas distribution tube 12 to be cleaned. Beyond the gas distribution tube 12 is a downstream conduit 52 connectable to the second end 54 of the gas distribution tube 12 via a second flexible hose 56 also via a conventional quick-disconnect fitting. The downstream conduit 52 has therein a valve 58 for selectively directing fluid therein passing from the gas distribution tube 12 to either the first reservoir structure 16 or to the sampling port 60 for release and external collection for testing. A drip pan 62 with a split cover member 65 functions as a liquid collector and is situated beneath the gas distribution tube 12 such that any spilled solvent is captured and returned via a connection 66 to the portion of the downstream conduit 52 leading into the first reservoir structure 16. A selectively openable exit conduit 68 is situated to receive and selectively transport therethrough collected gas from within the first reservoir structure 16 to an exit port 70.

Operability of the portable flushing apparatus 10 proceeds as now described. Specifically, an operator wheels the apparatus 10 to a site near an aircraft and retrieves from the aircraft the gas distribution tubes 50 requiring cleaning. The first end 48 and second end 54 of one tube 12 at a time are respectively connected to the quick disconnect fittings of the hoses 46, 56 and the first pump 22 is activated to cause solvent from the first reservoir structure 16 to flow through the first conduit 20. The first input port of the first three-way valve 26 is placed in an open mode such that the solvent flows therethrough and through the third conduit 36 to the first input port of the second three-way valve 38. This first input port of the second three-way valve 38 is placed in the open mode such that the solvent flows through the second three-way valve 38 and into and through the gas distribution tube 12 for a period generally of 15 to 20 minutes. During this time, the valve 58 of the downstream conduit 52 is set to direct the solvent to the first reservoir structure 16. It is here noted that, because used solvent is thus returned to the first reservoir structure 16, the filter 24 as earlier identified serves to remove untoward particulate that may be present in the solvent used for the initial flush. After this initial flushing, the first input port of the first three-way valve 26 and the first input port of the second three-way valve 38 are closed to terminate solvent delivery from the first reservoir structure 16. Thereafter, upon connecting the first end of the gas supply conduit 40 to a gas supply line delivering nitrogen gas, the second input port of the second three-way valve 38 is placed in the open mode to thereby permit nitrogen to flow through the gas distribution tube 12 for purging. Because the valve 58 of the downstream conduit 52 remains set to direct flow to the first reservoir structure 16, the purging gas is delivered to the first reservoir structure 16. Upon purge completion, the second input port of the second three-way valve 38 is closed to thereby terminate gas flow. Simultaneously, the exit conduit 68 is opened to transport therethrough from the first reservoir structure 16 collected nitrogen gas disposed above the level of liquid solvent therein to the exit port 70 for downstream carbon filter treatment.

Final cleansing of the gas distribution tube 12 is accomplished by directing the second solvent from the second reservoir structure 30 through the gas distribution tube 12. This final flushing is accomplished by placing the second input port of the first three-way valve 26 and the first input port of the second three-way valve 38 in open modes and activating the second pump 34 to thereby cause the second solvent to flow through the second conduit 28 and thereafter through the first and second three-way valves 26, 38 for entry into and through the gas distribution tube 12. Because the second solvent is used only once, no solvent filtration occurs. During this final flush, which typically lasts for one to two minutes, the valve 58 of the downstream conduit 52 is first set to direct flow to the first reservoir structure 16, and thereafter is set to direct flow to the sampling port 60 for release and external collection to test for non-volatile residue. Negligible or zero non-volatile residue means that the gas distribution tube 12 is clean and acceptable for use. Thereafter, the second input port of the first three-way valve 26 and the first input port of the second three-way valve 38 are closed and the second pump 34 is deactivated to cease solvent flow, while the valve 58 of the downstream conduit 52 is once again set to direct flow to the first reservoir structure 16. The purging gas is delivered to the first reservoir structure 16. The second input port of the second three-way valve 38 is placed in the open mode to thereby permit nitrogen to flow through the gas distribution tube 12 the purging gas is delivered to the first reservoir structure 16. Upon purge completion, the second input port of the second three-way valve 38 is closed to thereby terminate gas flow. Simultaneously, the exit conduit 68 is opened to once again transport therethrough from the first reservoir structure 16 collected nitrogen gas disposed above the level of liquid solvent therein to the exit port 70 for downstream carbon filter treatment. Finally, the cleaned gas distribution tube 12 is removed and capped on each end for return to the aircraft, and the entire operation is repeated for second and subsequent gas distribution tubes in need of cleaning.

What is claimed is:

1. A portable flushing apparatus for cleaning an interior of a gas distribution tube, the apparatus comprising:

a) a first reservoir structure for housing a first solvent, said first reservoir structure having a first conduit leading therefrom in communication with a first end of the gas distribution tube for transporting fluid therein for selective delivery to the interior of said tube;

b) a second reservoir structure for housing a second solvent, said second reservoir structure having a second conduit leading therefrom in communication with the first end of the gas distribution tube for transporting fluid therein for selective delivery to the interior of said tube;

c) a gas supply conduit having a first end connectable to a gas supply line and a second end in communication with a first end of the gas distribution tube for transporting gas in the conduit for selective delivery to the interior of said tube;

d) a sampling port; and e) a downstream conduit in communication with a second end of the gas distribution tube for transporting fluid therefrom selectively for collection in a collection vessel or for release through the sampling port.

2. A portable flushing apparatus as claimed in claim 1 wherein the collection vessel is the first reservoir structure.

3. A portable flushing apparatus as claimed in claim 2 additionally comprising an exit conduit situated to receive and selectively transport therethrough collected gas from within the first reservoir structure to an exit port.

4. A portable flushing apparatus as claimed in claim 2, additionally comprising a liquid collector situated to be beneath the gas distribution tube during flushing thereof for capturing any spilled solvent.

5. A portable flushing apparatus as claimed in claim 1 additionally comprising a liquid collector situated to be beneath the gas distribution tube during flushing thereof for capturing any spilled solvent.

6. A portable flushing apparatus as claimed in claim 1 additionally comprising a wheeled carrier.

7. A portable flushing apparatus for cleaning an interior of a gas distribution tube, the apparatus comprising:
   a) a first three-way valve, a second three-way valve, and a sampling port;
   b) a first reservoir structure for housing a first solvent, said first reservoir structure having a first conduit leading therefrom for transporting fluid therein and terminating at a first distal end connected to a selectively openable and closable first input port of the first three-way valve;
   c) a second reservoir structure for housing a second solvent, said second reservoir structure having a second conduit leading therefrom for transporting fluid therein and terminating at a second distal end connected to a selectively openable and closable second input port of the first three-way valve;
   d) a third conduit leading from a selectively openable and closable outlet port of the first three-way valve to a selectively openable and closable first input port of the second three-way valve;
   e) a gas supply conduit having a first end connectable to a gas supply line and a second end connected to a selectively openable and closable second input port of the second three-way valve;
   f) an outlet port leading from the second three-way valve for communication with a first end of the gas distribution tube; and
   g) a downstream conduit for communication with a second end of the gas distribution tube, said downstream conduit having therein a valve for selectively directing fluid therein to the first reservoir structure or to the sampling port.

8. A portable flushing apparatus as claimed in claim 7 additionally comprising a liquid collector situated to be beneath the gas distribution tube during flushing thereof for capturing any spilled solvent, said collector in communication with the first reservoir structure for returning said spilled solvent thereto.

9. A portable flushing apparatus as claimed in claim 7 additionally comprising an exit conduit situated to receive and selectively transport therethrough collected gas from within the first reservoir structure to an exit port.

10. A portable flushing apparatus as claimed in claim 7 additionally comprising a wheeled carrier.

\* \* \* \* \*